(12) United States Patent
Rubin et al.

(10) Patent No.: US 8,795,438 B2
(45) Date of Patent: Aug. 5, 2014

(54) STETHOSCOPE DISINFECTION MONITORING AND REPORTING SYSTEM

(75) Inventors: Keith Rubin, Fort Lauderdale, FL (US); Michael R. Cole, Stratham, NH (US); James M. Sellers, Portsmouth, NH (US)

(73) Assignee: Seedlings Life Science Ventures, LL., New York, NY (US)

( * ) Notice: Subject to any disclaimer, the term of this patent is extended or adjusted under 35 U.S.C. 154(b) by 785 days.

(21) Appl. No.: 12/660,024

(22) Filed: Feb. 18, 2010

(65) Prior Publication Data

US 2011/0197921 A1   Aug. 18, 2011

(51) Int. Cl.
- *B08B 3/00* (2006.01)
- *A61L 2/28* (2006.01)
- *A61B 19/00* (2006.01)

(52) U.S. Cl.
CPC .............. *A61L 2/28* (2013.01); *A61L 2202/24* (2013.01); *A61B 19/34* (2013.01); *A61L 2202/17* (2013.01); *A61L 2202/14* (2013.01); *A61B 2019/448* (2013.01)
USPC ..................................................... 134/56 R

(58) Field of Classification Search
None
See application file for complete search history.

(56) References Cited

U.S. PATENT DOCUMENTS

| | | | |
|---|---|---|---|
| 2,604,650 | A | 7/1952 | Mottelson |
| 4,002,009 | A | 1/1977 | Tolosa et al. |
| 4,210,974 | A | 7/1980 | Stoltzman |
| 4,449,976 | A | 5/1984 | Kamen |
| 4,701,968 | A | 10/1987 | Stoltzman |
| 4,871,046 | A | 10/1989 | Turner |
| 4,953,999 | A | 9/1990 | Rivers |
| 5,048,549 | A | 9/1991 | Hethcoat |
| 5,114,670 | A | 5/1992 | Duffey |
| 5,185,532 | A | 2/1993 | Zabsky et al. |
| 5,448,025 | A | 9/1995 | Stark et al. |
| 5,466,897 | A | 11/1995 | Ross et al. |
| D375,161 | S | 10/1996 | Hart |
| 5,641,464 | A | 6/1997 | Briggs, III et al. |

(Continued)

FOREIGN PATENT DOCUMENTS

| | | |
|---|---|---|
| CN | 148125 A | 3/2004 |
| CN | 101674898 A | 3/2010 |

(Continued)

OTHER PUBLICATIONS

Dix, et al., "Environmental Surface Cleaning First Defense Against Infectious Agents." http://www.vpico.com/articlemanager/printerfriendly.aspx?article=60960; Dec. 2, 2006; 7pg.

(Continued)

*Primary Examiner* — Jason Ko
(74) *Attorney, Agent, or Firm* — Malloy & Malloy, P.L.

(57) ABSTRACT

A stethoscope disinfection monitoring and reporting system structured and configured to track, monitor and report the cleaning, disinfecting, and/or sterilizing of the head portion of a stethoscope is presented. The system comprises a stethoscope cleaning assembly cooperatively structured and configured to clean the head portion of the stethoscope, for instance, via the application of a cleaning fluid or solution thereto. The system further comprises a monitoring device and a cooperatively structured and disposed reader assembly. The monitoring device may be unique to, or otherwise serve to identify, the stethoscope. The reader assembly is structured and disposed to detect, identify, and record data pertaining to the monitoring device and/or stethoscope upon cleaning the head portion, or otherwise upon disposition of the head portion into a cleaning relation with the stethoscope cleaning assembly.

24 Claims, 6 Drawing Sheets

(56) References Cited

U.S. PATENT DOCUMENTS

| | | | |
|---|---|---|---|
| 5,686,706 A | 11/1997 | Wurzburger | |
| 5,692,657 A | 12/1997 | Kilo et al. | |
| 5,808,244 A | 9/1998 | Knight et al. | |
| 5,813,992 A | 9/1998 | Henwood | |
| 5,865,551 A | 2/1999 | Lalli et al. | |
| 5,892,233 A | 4/1999 | Clement | |
| 5,925,021 A | 7/1999 | Castellano et al. | |
| 6,018,835 A | 2/2000 | Schonfeld | |
| 6,019,187 A | 2/2000 | Appavu | |
| D425,353 S | 5/2000 | Foy | |
| 6,206,134 B1 | 3/2001 | Stark et al. | |
| D445,185 S | 7/2001 | Najmi | |
| 6,461,568 B1 | 10/2002 | Eckhardt | |
| 6,467,568 B1 | 10/2002 | Kemper | |
| 6,484,918 B1 | 11/2002 | Lefebvre | |
| 6,575,917 B2 | 6/2003 | Giroux et al. | |
| 6,643,998 B1 | 11/2003 | Curtis et al. | |
| 7,117,971 B1 | 10/2006 | Cornacchia | |
| 7,182,117 B2 | 2/2007 | Abe et al. | |
| 7,258,125 B2 | 8/2007 | Holbrook | |
| 7,282,186 B2 | 10/2007 | Lake, Jr. et al. | |
| 7,287,426 B2 | 10/2007 | Frank | |
| 7,406,973 B1 | 8/2008 | Perlman et al. | |
| 7,424,929 B1 | 9/2008 | Martinez | |
| 7,469,769 B1 | 12/2008 | Hmayakyan et al. | |
| 7,503,335 B2 | 3/2009 | Perlman et al. | |
| 7,614,478 B2 | 11/2009 | Hmayakyan et al. | |
| 7,636,445 B2 | 12/2009 | Yoshimine | |
| D621,935 S | 8/2010 | Cole et al. | |
| 7,866,908 B2 | 1/2011 | Perlman et al. | |
| 7,942,597 B2 | 5/2011 | Perlman et al. | |
| 8,057,117 B2 | 11/2011 | Perlman et al. | |
| D652,142 S | 1/2012 | Perlman et al. | |
| 2002/0146343 A1 | 10/2002 | Jenkins et al. | |
| 2002/0198564 A1 | 12/2002 | Pichon et al. | |
| 2004/0090333 A1* | 5/2004 | Wildman et al. | 340/573.1 |
| 2004/0258560 A1 | 12/2004 | Lake, Jr. et al. | |
| 2005/0214185 A1 | 9/2005 | Castaneda | |
| 2005/0236579 A1 | 10/2005 | Jenkins et al. | |
| 2005/0254992 A1 | 11/2005 | Jenkins et al. | |
| 2007/0080017 A1 | 4/2007 | Stickley | |
| 2007/0202005 A1* | 8/2007 | Maschke | 422/3 |
| 2007/0256753 A1 | 11/2007 | Riley | |
| 2007/0261185 A1 | 11/2007 | Guney et al. | |
| 2008/0019889 A1 | 1/2008 | Rogers et al. | |
| 2008/0131332 A1 | 6/2008 | Nguyen et al. | |
| 2009/0144918 A1 | 6/2009 | Perlman et al. | |
| 2009/0273477 A1 | 11/2009 | Barnhill | |
| 2010/0116300 A1 | 5/2010 | Perlman et al. | |
| 2010/0116841 A1 | 5/2010 | Perlman et al. | |
| 2011/0197921 A1 | 8/2011 | Rubin et al. | |
| 2012/0117792 A1 | 5/2012 | Perlman et al. | |
| 2012/0125377 A1 | 5/2012 | Perlman et al. | |

FOREIGN PATENT DOCUMENTS

| | | |
|---|---|---|
| CN | 101678131 A | 3/2010 |
| EP | 2 131 967 | 12/2009 |
| EP | 2 155 265 | 2/2010 |
| JP | 2010522058 | 7/2010 |
| JP | 2010522062 | 7/2010 |
| WO | WO 02/094326 A1 | 11/2002 |
| WO | WO 2008/118311 A2 | 10/2008 |
| WO | WO 2008/118401 A2 | 10/2008 |
| WO | WO 2011/103090 A1 | 8/2011 |

OTHER PUBLICATIONS

Virgo Publishing., "A Clean Sweep: Surface Cleaning in the Healthcare Environment." http://www.vpico.com/articlemanager/printerfriendly.aspx?article=60253; Dec. 1, 2004; 3 pg.

McCaughey., "Coming Clean—New York Times." http://www.nytimes.com/2005/06/06/opinion/06mccaughey.html?ei=5088&en=d591e517f . . . ; Dec. 2, 2006; 1 pg.

Sharmila et al., "Stethoscope and Nosocomial Infection," Indian Journal of Pediatrics, 2000; 67 (3): 197-199.

Marinella, et al., "The Stethoscopy: A Potential Source of Nosocomial Infection?," vol. 157(7), Apr. 14, 1997, pp. 786-790, Mar. 30, 2006.

Jones, et al., "Stethoscopes: A Potential Vector of Infection?" Annals of Emergency Medicine. 26:Sep. 3, 1995; 296-299.

CDC, "Contact Precautions from the Guidelines for Isolation Precautions in Hospitals (Jan. 1996)." http://www.cdc.gov/ncidod/dhqp/gl_isolation_contact.html; Dec. 2, 2006; 2 pg.

CDC, "Standard Precautions from the Guidelines for Isolation Precautions in Hospitals (Jan. 1996)." http://www.cdc.gov/ncidod/dhqp/gl_isolation_standar.html; Dec. 2, 2006; 2 pg.

Schneider, "Report of the Counsil on Science and Public Health—CSAPH's Sunet Review of 1996 House Policies".

"American Medical AssociationProceedings of the House of Delegates," 50th Interim Meeting, Dec. 8-11, 1996. Resolution 501. Policy H-440. 908.

* cited by examiner

STETHOSCOPE DISINFECTION MONITORING AND REPORTING SYSTEM

BACKGROUND OF THE INVENTION

1. Field of the Invention

The present invention is generally directed to a system structured and configured to track, monitor and report the cleaning, disinfecting, and/or sterilizing of the head portion of a stethoscope. In particular, the system comprises a stethoscope cleaning assembly cooperatively structured and configured to clean the head portion of the stethoscope, for instance, via the application of a cleaning fluid, solution, or barrier thereto. The system further comprises a monitoring device and a cooperatively structured and disposed reader assembly. The monitoring device is unique to, or otherwise serves to identify, the stethoscope, an associated physician, and/or a physician's identification tag. The reader assembly is structured and disposed to detect, identify, and record data pertaining to the monitoring device and/or stethoscope upon cleaning the head portion, or otherwise upon disposition of the head portion into a proximate or cleaning relation with the stethoscope cleaning assembly, as well storing collected identification or cleaning data or transmitting the data via wired or wireless means to a central or remote date storage and collection system.

2. Description of the Related Art

As is well recognized in the medical profession, and commonly acknowledged by many individuals not directly associated with the medical care industry, the use of a stethoscope by health care providers is routine. As typically applied, the head and/or diaphragm portion of the stethoscope is normally placed in direct contact with the skin of the patient at various locations over the patient's body. In applying the stethoscope in this manner, and in particular in situations where the stethoscope head or diaphragm may be exposed to the bodily fluids of the patient, the transmission of infection, bacteria, diseases, etc., from patient to patient is a distinct possibility.

While some stethoscopes are structured for disposal after each use, a great number of stethoscopes are non-disposable and are intended for continued and repeated use. This latter category of stethoscopes are typically carried by the health care provider on a substantially continuous basis and used repeatedly and successively for examination of multiple patients. In order to avoid the transmission of infection, bacteria, diseases, etc., from patient to patient when using this latter category of instruments, attempts have been made to facilitate at least a minimal cleaning and/or disinfecting of the head portion of the stethoscope. However, because of time demands, emergency situations and other situations which frequently occur, a health care provider or physician may skip a cleaning or only perform a minimal cleaning of the instrument on an occasional basis.

To better appreciate the requirements necessary to accomplish a proper cleaning and disinfecting of the stethoscope head, it is important to understand the various structural components thereof and their intended use during an examination procedure. More specifically, the stethoscope head typically includes a diaphragm portion comprising a thin disk of appropriate material that is disposed in confronting relation to a patient's skin. As such, the diaphragm forms an acoustical seal with the contacted portion of the patient. In addition, the head portion also includes a ring or rim which retains or is otherwise disposed and structured for supportive engagement with the diaphragm. Finally, the stethoscope head includes a base or spine of the head formed of metal or other composite base material that is structured to serve as the location where the user may grasp the device comfortably, usually with a thumb and one or two fingers of a single hand. A magnification and transmission of the sounds detected during the examination procedure is thereby accomplished. In addition, an appropriate conduit or tubing which may be formed of a rubber or like material is secured to the head and extends outwardly there from so as to interconnect the ear pieces of the stethoscope to the head portion.

Health care associated (nosocomial) infections are a growing concern for hospitals in the United States and worldwide. Approximately, two million patients admitted to U.S. hospitals each year acquire a health care associated infection. Of these, more than seventy thousand will die. These infections add about $30 billion annually to U.S. healthcare cost. The transfer of pathogenic bacteria from one patient to another is a major cause of healthcare associated infections. This transfer may be facilitated by healthcare workers who do not adequately clean and disinfect their hands and/or patient-care equipment after patient contact.

Stethoscopes harbor pathogenic bacteria. Bacteria may be transferred intact to human skin directly from a stethoscope diaphragm. The stethoscope diaphragm and rim (the portions of the stethoscope that directly contact the patient's skin) may be adequately disinfected and cleaned by one or several wipes with a prepackaged isopropyl alcohol pad or swab. However, the majority of healthcare workers do not clean or disinfect their stethoscope after each patient encounter. Less than half of workers clean their stethoscopes daily or even weekly.

The Centers for Disease Control and Prevention recommends that healthcare workers dedicate the use of non-critical care equipment to a single patient. If this is not possible, then it is recommended that these items be adequately cleaned and disinfected before being used on another patient. These recommendations are specifically for patients that are known or suspected to harbor pathogenic organisms. However, the Centers for Disease Control and Prevention also recommends that for all patients receiving care in a hospital, an item of patient care equipment must not be reused on another patient until it has been cleaned and reprocessed appropriately. The American Medical Association has also resolved that healthcare providers should frequently clean their stethoscopes to prevent the spread of nosocomial infections. In particular, it recommended that even in the event the stethoscope or other device does not come into contact with a patient, it should be thoroughly cleaned and disinfected at least once every three hours.

In light of the critical need for health care providers to timely and adequately clean and disinfect his or her stethoscope or other medial device, there is a need for a system that is structured and configured to track, monitor, and report the cleaning of the medical devices. In particular, there is a need to monitor and track a physician's cleaning activities relating to the stethoscope.

SUMMARY OF THE INVENTION

The present invention is generally directed to a system structured and configured to track, monitor and report the cleaning, disinfecting, and/or sterilizing of the head portion of a stethoscope. In particular, the system comprises a stethoscope cleaning assembly cooperatively structured and configured to clean the head portion of the stethoscope, for instance, via the application of a cleaning fluid or solution thereto.

As generally used, it is recognized that the terms "clean" and/or "disinfect" may be strictly interpreted as referring to different procedures intended to accomplish different results.

By way of example, the term "clean" and "cleanse" may be typically used in situations where it is intended to remove dirt, impurities, debris, contaminants, etc. In contrast, the term "disinfect" may be used to remove or kill harmful microorganisms or render them harmless. However, as used herein the terms "clean", "cleanse" "cleaning fluid" and/or "cleaning action" are meant to encompass all of the above cleaning and disinfecting procedures. The category or degree of "cleaning" in a practical application of the present invention will be at least partially dependent on the cleaning fluid to which the head portion of the stethoscope is exposed and/or the particular application or transfer of a barrier to the head portion of the stethoscope.

By way of example, the cleaning assembly of the various embodiments of the present invention may incorporate the use of a cleaning fluid comprising an alcohol based composition. More specifically, the cleaning fluid used in the operation of the present invention may include, but is not limited to, an antimicrobial fluid and/or an alcohol-based solution such as isopropyl or ethyl alcohol in standard concentrations. Moreover, the cleaning fluid is applied in an appropriate manner to the exposed surfaces of the diaphragm, supportive rim and possibly other adjacent or contiguous portions associated with the head portion of the stethoscope. Therefore, other factors to be considered are the type of wiping, scrubbing, brushing or other types of physical engagement or contact to which the head portion is subjected during the cleaning procedure.

In addition, the cleaning assembly, as used herein, may comprise a plurality of barriers, films, caps, or covers removably disposable in a covering relation to the exposed portion(s) of the stethoscope. In particular, the barriers may include a flexible, rigid, or partially rigid material structured to removably adhere to the head portion of the stethoscope and may be sterilized and/or include a disinfecting composition incorporated therein or thereon in any appropriate manner. As such, the exposed surfaces or other portions of the stethoscope head which would normally come into contact with a patient will be covered and/or at least partially cleansed or disinfected such that the actual surface of the stethoscope head will not contact or engage the patient or other individual. Once the examination or treatment of the patient is completed, the attached protective barrier may be easily removed and discarded in any safe, appropriate manner.

Furthermore, the cleaning assembly may simply include a box or other container of a plurality of pre-packaged cleaning cloths, wipes, pads or other like devices structured for manual cleaning of the head portion. For instance, a medical personnel may select or grab a cloth, wipe, etc., from the cleaning assembly and manually wipe or clean the stethoscope. The various cloths or wipes may comprise or be treated with an appropriate cleaning fluid.

Accordingly, with the above acknowledgement to the strict definitions of the above terms, the use of the term "clean", "cleaning", and/or "cleaning action" are also meant to encompass all of the above noted procedures, the various types of cleaning fluids capable of being used as well as any of a variety of different types of physical engagement or contact applied to the portions of the head of the stethoscope being treated.

As described in greater detail herein, the stethoscope disinfection monitoring and reporting system further comprises at least one or a plurality of hygienic monitoring devices, each of which may be unique to, or otherwise serve to identify, a particular stethoscope, an associated physician, and/or a physician's identification tag. Moreover, the various embodiments further comprise a cooperatively structured and/or disposed reader assembly connected, either fixedly, movably, or removably, to the cleaning assembly. In particular, the hygienic monitoring device is at least momentarily disposed in a proximate and communicative relation with the reader assembly, for instance, while the head portion of the stethoscope is disposed in a proximate and/or cleaning relation with the cleaning assembly. More specifically, upon disposition of the head portion in the cleaning relation with the cleaning assembly, the reader assembly is activated and/or structured to detect and identify the proximately disposed hygienic monitoring device. The monitoring device and the reader assembly are communicatively disposed with one another at least until appropriate detection, identification, or transfer of data there between as described in accordance with the various embodiments of the present invention.

Further, the hygienic monitoring device is disposed in a proximate relation with the reader assembly when the monitoring device is within a predetermined communication range associated with the particular devices used and/or a pre-selected or predefined distance of a few inches, a few feet, and/or within the same room or communicative vicinity. For instance, as described in greater detail below, the hygienic monitoring device 30 and the cooperatively structured reader assembly 40 may comprise a plurality of structures, devices, assemblies, or configurations structured to facilitate implementation of the present invention in the intended manner, and may thus establish an appropriate one-way or two-way wireless or other communicative link.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

As shown in the accompanying drawings, the present invention is directed to a stethoscope disinfection monitoring and reporting system, generally referenced as 10.

Figure 1:
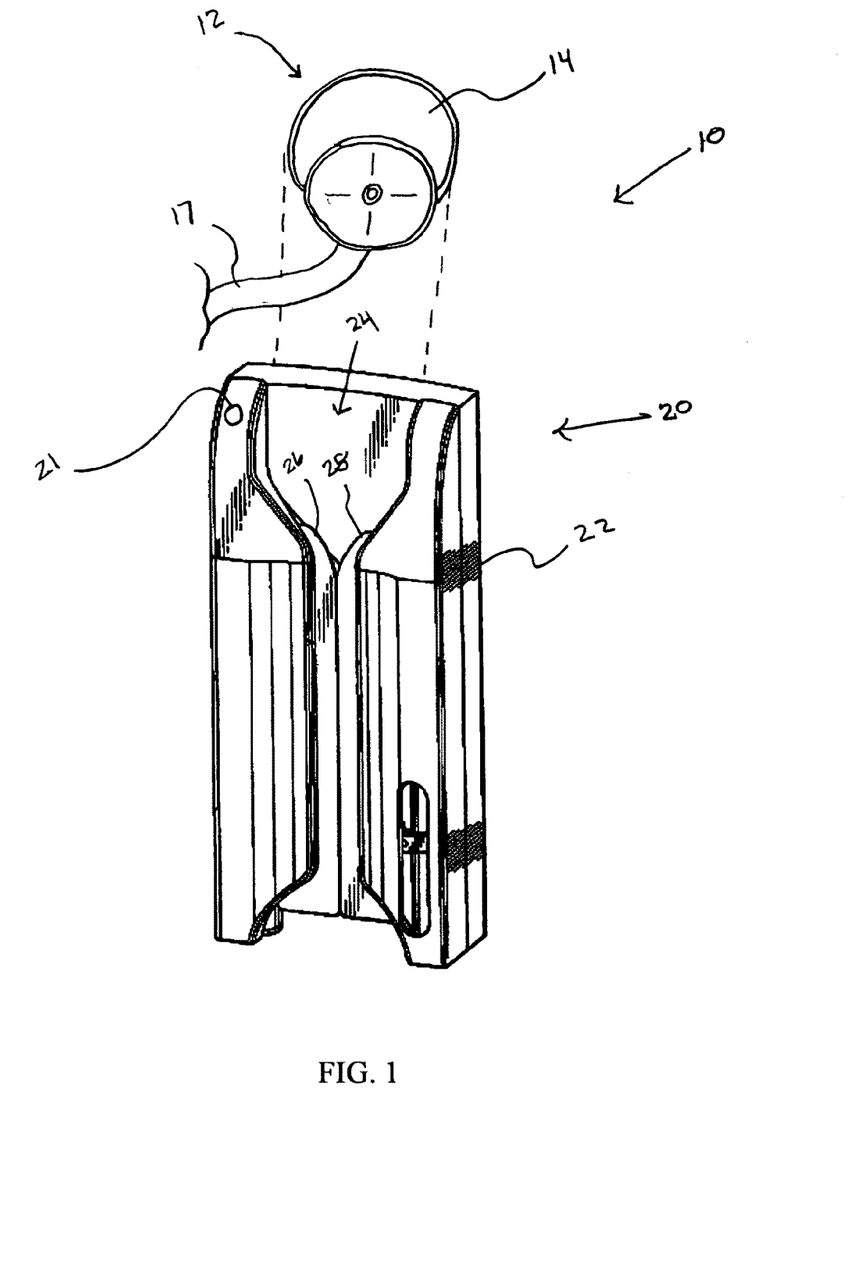
FIG. 1 is a exterior frontal perspective view of at least one embodiment of the stethoscope disinfection monitoring and reporting system disclosed and described herein.
Figure 2:
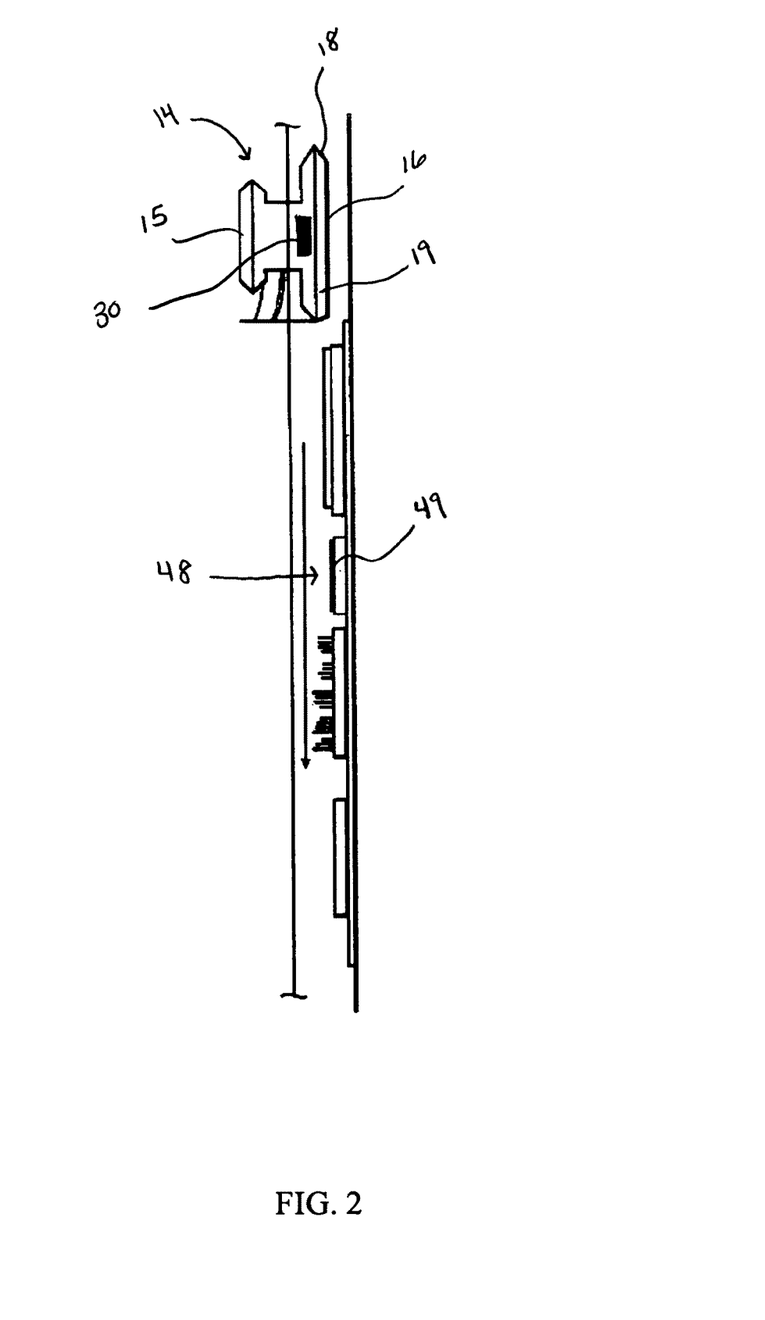
FIG. 2 is partial cut away side schematic representation of the system as disclosed and described in at least one embodiment of the present invention.

In particular, as shown in FIG. 1, the system 10 of the present invention comprises a cleansing assembly 20 including a housing 22. As presented herein, the cleaning assembly 20 of the various embodiments is structured and configured to at least partially "clean" a head portion 14 of a stethoscope 12. For instance, the housing 22 of at least one embodiment comprises an at least partially hollow interior of sufficient dimension and configuration to contain a plurality of operative components. As an example, the cleaning assembly 20 as used and referred to in accordance with the present invention may include the device(s) shown and described in U.S. patent application Ser. Nos. 11/728,207 (now U.S. Pat. No. 7,406,973), Ser. No. 12/079,077 (now U.S. Pat. No. 7,503,335), Ser. Nos. 12/316,123, 12/584,276, and 12/584,061, the contents of each are hereby incorporated by reference in their entirety. Particularly, the cleaning assembly 20 is specifically structured and configured to "clean" the diaphragm, supportive rim and other exposed areas of the head portion 14 which are brought in direct contact with a patient or a patient's body. More specifically, the head portion 14, as represented in FIG. 2, for example, comprises a diaphragm 16 and a supporting or surrounding rim portion 18 generally associated with an exposed face or patient contacting portion 19. Additionally, the head portion 14 of the stethoscope 12 comprises a spine or stem portion 15 which is generally structured to facilitate a user to grasp onto with a single hand during operative use.

In addition, the cleaning assembly 20 may comprise a fluid supply and/or at least one but possibly a plurality of fluid chambers or reservoirs structured to contain a quantity of cleaning fluid therein. For exemplary purposes only, the fluid supply may comprise an alcohol-based cleaning fluid and/or anti-microbial liquid. Either way, the cleaning fluid is formulated to effect a cleaning, disinfecting, and/or sterilizing action on exposed areas of the head portion 14.

As will become apparent from the following discussion, however, other cleaning assemblies 20 cooperatively structured and configured to "clean" the head portion 14 of the stethoscope 12 are contemplated and included in the described invention. As an example, the cleaning assembly 20, as used herein, may also or instead comprise a plurality of barriers, films, caps, or protective coverings disposable in a covering relation to the head portion of the stethoscope 12. In particular, the barriers may include a flexible, rigid, or partially rigid material structured to removably adhere to the head portion 14 of the stethoscope 12, and may be sterilized and/or include a disinfecting composition incorporated therein or thereon. As such, the exposed surfaces or other portions of the stethoscope 12 which would normally come into contact with a patient may be covered and/or at least partially cleansed or disinfected such that the actual surface of the stethoscope head 14 will not contact or engage the patient or other individual. Once the examination or treatment of the patient is completed, the attached protective barrier may be easily removed and discarded in any safe, appropriate manner.

In addition, the cleaning assembly 20 may include a box or other container or dispenser of a plurality of cleaning cloths, wipes, or other like devices structured for manual cleaning of the head portion 14 of the stethoscope 12. For instance, a medical personnel may select or grab a cloth, wipe, etc., from the cleaning assembly 20 and manually wipe or clean the stethoscope 12. The various cloths or wipes may comprise or be treated with an appropriate cleaning fluid.

Accordingly, the cleaning assembly 20, as used herein, includes any device or assembly which is structured to appropriately "clean" the head portion 14, at least while the head portion 14 is disposed in a cleaning relation to the cleaning assembly 20. As used herein, disposition of the head portion 14 in a cleaning relation with the cleaning assembly 20 includes positioning or otherwise orienting the head portion 14 or cleaning assembly 20 in a manner such that the cleaning assembly 20 will "clean" the head portion and/or apply a quantity of cleaning fluid and/or a film or barrier thereto. As one example, and as shown in exemplary embodiments of FIGS. 1 and 2, the cleaning assembly 20 may comprise a receiving portion 24 cooperatively structured and configured to receive the head portion 14 of the stethoscope 12 therein and apply a quantity of cleaning fluid and/or a removable barrier thereto. The receiving portion 24 may comprise, for instance, a channel having an entrance and an exit defining a path of travel of the head portion 14 as described in greater detail in the U.S. patent applications and U.S. patents incorporated herein by reference above. Of course, other receiving portions 24 and other cleaning assemblies 20 are contemplated and thus the cleaning assembly 20 of the present invention may, but need not comprise, for example, a path of travel, a channel, and/or an entrance and exit portion.

Furthermore, the stethoscope disinfection monitoring and reporting system 10 of the various embodiments of the present invention comprises a hygienic monitoring device 30, and a cooperatively structured reader assembly 40. In particular, the reader assembly is connected, either fixedly, movably, or removably, to the cleaning assembly 20, and in particular, the housing 22 thereof. As will be described in greater detail below, the hygienic monitoring device 30 is connected to or otherwise associated with a stethoscope, physician, or health care provider, and is at least momentarily disposed in a proximate and communicative relation with the reader assembly 40, for instance, upon activating the reader assembly 40 and/or while the head portion 14 of the stethoscope is disposed in the cleaning relation with the cleaning assembly 20. More specifically, upon disposition of the head portion 14 in the cleaning relation with the cleaning assembly 20, for example, upon disposing the head portion 14 within channel 24, the reader assembly 40 is structured to detect and identify the proximately disposed hygienic monitoring device 30.

In yet another embodiment, however, the reader assembly 40 is structured to detect, identify, or otherwise communicate with a monitoring device 30 merely disposed in a proximate relation thereto, and thus the stethoscope need not be disposed in the cleaning relation with the cleaning assembly 20 to initiate or activate a communication link between the reader assembly 40 and monitoring device 30. In particular, the hygienic monitoring device is disposed in a proximate relation with the reader assembly when the monitoring device is within a predetermined communication range associated with the particular devices used and/or a pre-selected or pre-defined distance of a few inches, a few feet, and/or within the same room or communicative vicinity.

As such, the hygienic monitoring device 30 and the cooperatively structured reader assembly 40 may comprise a plurality of structures, devices, assemblies, or configurations structured to facilitate implementation of the present invention in the intended manner. As on example, the hygienic monitoring device 30 and reader assembly 40 may comprise a cooperatively structured and disposed bar code and bar code reader, respectively, wherein the hygienic monitoring device 30 is disposed on the head portion 14 of the stethoscope 12 and the reader assembly 40 is cooperatively positioned and disposed on the cleaning assembly 20 so as to read the bar code or other hygienic monitoring device 30 upon disposition of the head portion 14 in the cleaning relation with the cleaning assembly 20.

In yet another embodiment, the hygienic monitoring device 30 is structured to establish short range wireless communication with the reader assembly 40 at least to the extent of generating a signaled communication from the monitoring device 30 to the reader assembly 40. For instance, the hygienic monitoring device 30 and/or reader assembly 40 may be implemented or function via 1-WIRE® connectors, smart buttons, BlueTooth, ZIGBEE®, etc. The wireless communication may be representative of informational data relating to the identity of the associated stethoscope 12, physician, health care provider, or health care identification badge, for example, as well as cleaning data determinative of compliance with predetermined cleaning requirements and/or the hygienic status of the stethoscope 12. Accordingly, the hygienic monitoring device 30 may comprise memory capabilities or a memory device structured to store the required stethoscope/health care identification and/or cleaning data. In at least one embodiment, the hygienic monitoring device 30 comprises a radio frequency identification ("RFID") device, or RFID tag, capable of operating at multiple frequencies including, low, high, or ultra high frequencies. Also, the hygienic monitoring device 30 may be active or passive in terms of having a self-contained power supply.

In addition, the reader assembly 40 of at least one embodiment comprises memory capabilities at least to the extent of recording and storing the informational data communicated thereto by the hygienic monitoring device 30 and/or other cleaning data generated by the reader assembly 40 and/or communicated by the hygienic monitoring device 30. For example, upon disposing the head portion 14 of the monitoring device 30 in a cleaning relation with the cleaning assembly 20, or otherwise upon cleaning the head portion 14 of the stethoscope 12 with the cleaning assembly 20, the hygienic monitoring device 30 and the reader assembly 40 are structured to initiate a communicative link with one another. Upon doing so, the cleaning data, which is structured to indicate the hygienic status of the stethoscope 12 or otherwise track the cleaning of the associated stethoscope 12, may be updated or otherwise modified. For instance, the cleaning data may determine or indicate the time and location of each cleaning of the associated stethoscope 12, identify the health care provider, etc. Coupled with the identification data, the hygienic status of the stethoscope 12, e.g., the frequency of cleaning and/or whether the stethoscope is clean or is need of cleaning, may be easily tracked and monitored. In at least one embodiment, the modified or updated identification/cleaning data is then saved on the hygienic monitoring device 30 and/or reader assembly 40 for future use and tracking.

Figure 4:
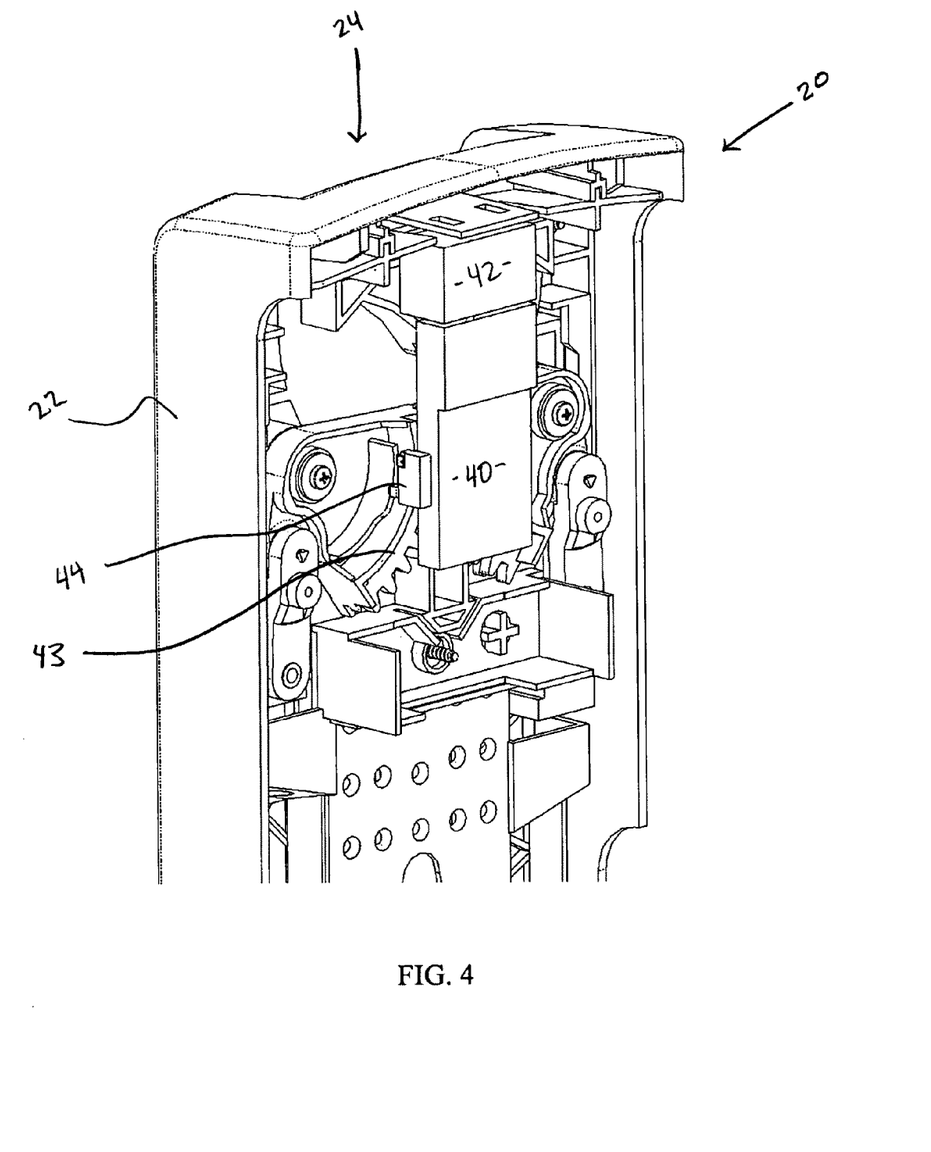
FIG. 4 is a partial rear cut away perspective view of a cleaning assembly disclosed and described in accordance with at least one embodiment of the present invention wherein the activation device is disposed in a operative position.
Figure 5:
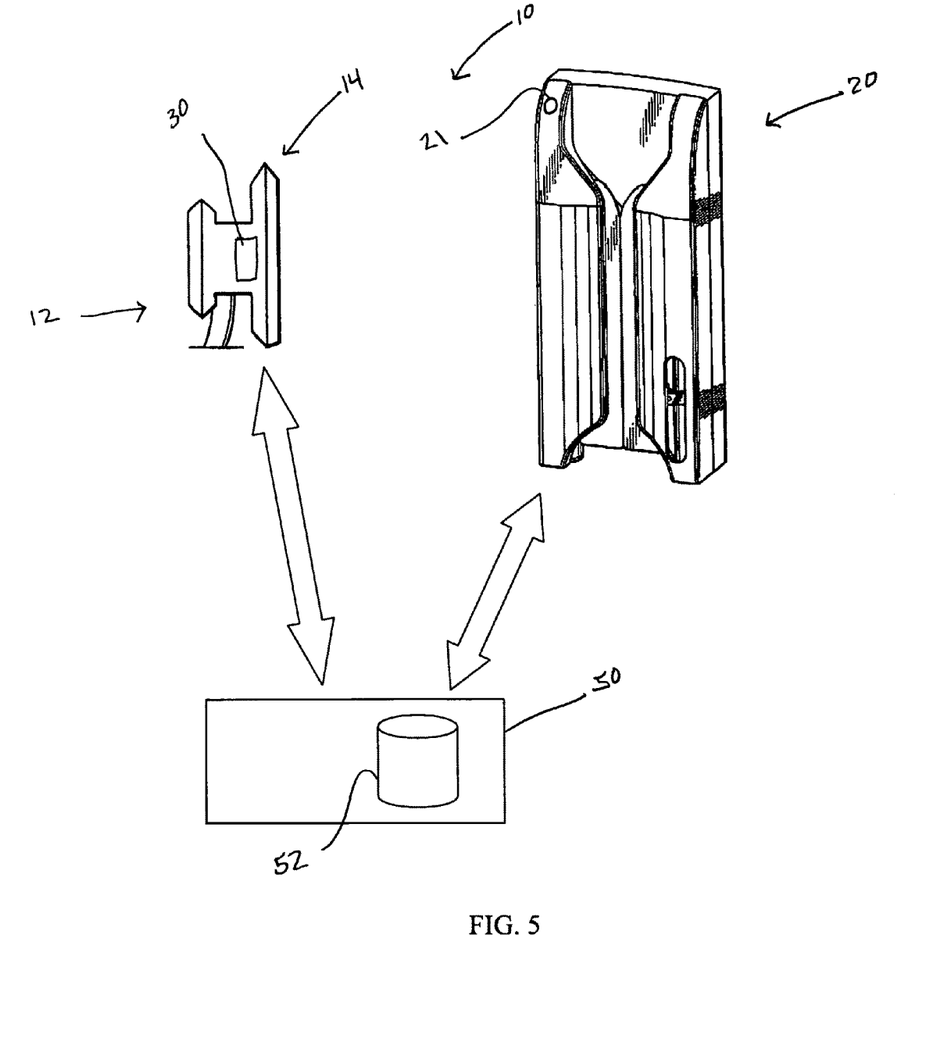
FIG. 5 is a schematic representation of at least one embodiment of the present invention comprising a remote data collection system.

Referring now to FIG. 5, additional operative features of at least one embodiment comprises a remote data collection system 50 comprising a storage assembly 52, including a database, hard drive, or other memory capabilities, structured to store and maintain the plurality of identification and cleaning data. In at least one embodiment, the cleaning assembly 20 and/or reader assembly 40 comprises a transmitter or wireless communication device 42 (shown in FIGS. 3 and 4) such that the cleaning assembly 20 and/or reader assembly 40 is disposable in a communicative relation with the remote data collection system 50. More in particular, the remote data collection system 50 of such an embodiment is at least disposable in a data receiving relation with the wireless communication device 42, wherein the wireless communication device 42 is structured to wirelessly communicate or transmit the plurality of identification and cleaning data thereto. For instance, the wireless communication device 42, reader assembly 40, and/or cleaning assembly 20 may be structured to automatically communicate or transmit the data to the remote data collection system 50 on a predetermined, preset, and/or periodic basis, such as, every hour, three times a day, once a day, after a certain predetermined number of cleanings, etc. Of course, the wireless communication device 42, reader assembly 40, and/or cleaning assembly 20 may instead or additionally be structured to automatically communicate or transmit the identification and/or cleaning data to the remote data collection system 50 after each cleaning of a stethoscope 12 or otherwise each time the data is collected, read, modified, and/or updated. Accordingly, the reader assembly 40 may, but need not comprise memory capabilities to the extent of storing the collected identification and/or cleaning data, and may thus automatically communicate or transmit the data to a remote location immediately upon receipt or collection of the data without the need to store the data on or at the reader assembly 40.

As illustrated in FIG. 1, the cleaning assembly 20 of at least one embodiment may comprise a verification indicator 21 in the form of a single or multi-colored LED structured to indicate that a successful cleaning has occurred, and/or that a successful communication between the hygienic monitoring device 30 and the reader assembly 40 has occurred, and that the appropriate data has been successfully stored and/or transmitted to the remote data collection system 50. Of course, the LED or other indicator 21 may instead or additionally signal a failed cleaning or communication link.

Additionally, however, in at least one embodiment, the hygienic monitoring device 30 is disposable in a communicative relation with the remote data collection system 50. For instance, and similar to the discussion above with regard to the wireless communication device 42, the hygienic monitoring device 30 may be structured to automatically or selectively communicate the data to the remote data collection system 50, for instance, periodically or upon modification of the data. For example, a physician, health care provider, etc., may be required or asked to upload the stethoscope identification and/or cleaning data to the remote data collection system 50 at the end of each day, week, month, etc., so the hygienic status of the associated stethoscope may be monitored and tracked appropriately. The hygienic monitoring device 30 may also be structured to automatically communicate or transmit the data to the remote data collection system 50 on a predetermined, preset, or periodic basis, such as, every hour, three times a day, once a day, after each stethoscope cleaning, etc.

In at least one embodiment, the hygienic monitoring device 30 is uniquely associated with a particular stethoscope 12, such that the system 10 of the present invention is capable of accurately monitoring, tracking and reporting the hygienic status of the each particular and individual stethoscope 12. For example, the hygienic monitoring device 30 may be programmed with stethoscope identification data, such as a particular serial number, and/or registered with the remote data collection system 50 or other database to link the hygienic monitoring device 30 with the associated stethoscope 12. In addition, the hygienic monitoring device 30 may be connected, either fixedly or removably, to the associated stethoscope, for instance at or near the head portion 12, on the tubing 17, or any other predetermined, selected, or appropriate location.

In yet another embodiment, however, the hygienic monitoring device 30 is uniquely associated with a physician, health care provider, and/or a health care identification badge 60. For instance, the hygienic monitoring device 30 may be structured in the form of an identification badge to be worn by a physician or other health care provider. In addition, the features, functions, and operative characteristics of the hygienic monitoring device 30 of the present invention may be incorporated into an existing identification badge 60 so as to minimize the number of additional badges, or ID tags worn by the health care provider at a given time.

Either way, the hygienic monitoring device 30 of one or more embodiments of the present invention may simply act as an identification tag for the associated stethoscope 12, and thus the stethoscope identification data programmed onto or otherwise associated with the monitoring device may not be subsequently modified or altered. Along these lines, in such an embodiment the stethoscope cleaning data determinative of compliance with predetermined cleaning requirements or otherwise determinative of the hygienic status of the stethoscope may be stored remotely from the monitoring device 30, such as on or at the remote data collection system 50 or on or at the reader assembly 40.

Figure 3:
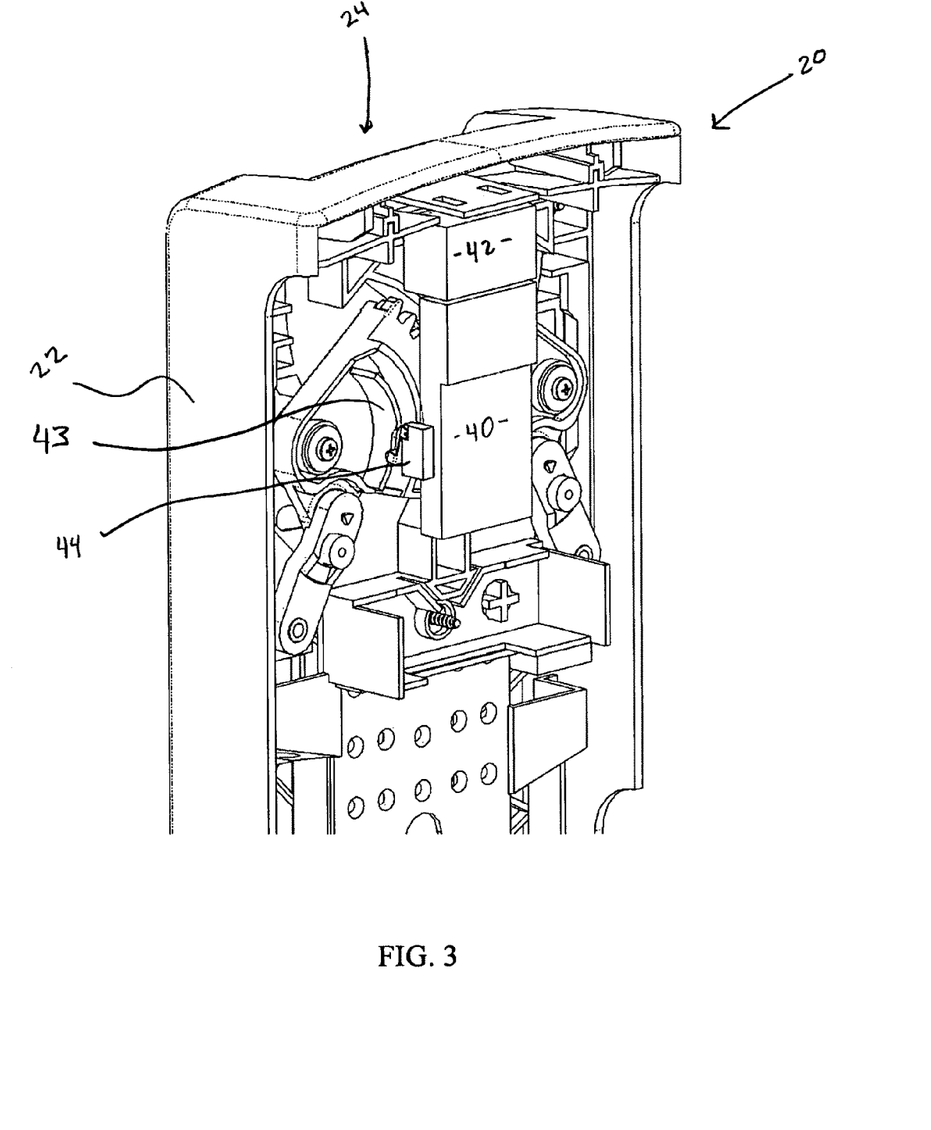
FIG. 3 is a partial rear cut away perspective view of a cleaning assembly disclosed and described in accordance with at least one embodiment of the present invention wherein the activation device is disposed in a non-operative position.

Referring now to FIGS. 3 and 4, at least one embodiment of the stethoscope disinfection monitoring and reporting system 10 comprises an activation device 44 disposable into and out of an operative and activating relation with the reader assembly 40. In particular, the activation device 44 may comprise a switch, micro-switch, or other connections or mechanisms structured to facilitate implementation of the present invention in the intended fashion. For instance, FIG. 3 illustrates the activation device 44 in a relaxed and/or non-activated position. In such a position, the reader assembly 40 is similarly structured to be in a relaxed or non-operative, sleeping state or mode. As such, while in a relaxed, non-operative or sleeping state, the reader assembly 40 will not establish a communicative relation with proximately disposed hygienic monitoring devices 30, for instance those within a predetermined range or otherwise within a range of communication with the reader assembly 40. Accordingly, when in a non-operative state, the reader assembly 40 will not detect or identify stethoscopes, physician identification badges, or hygienic monitoring devices 30 simply passing by, proximately located, or otherwise not being cleaned by the cleaning assembly 20.

However, upon disposition of the stethoscope 12 or head portion 14 thereof in a cleaning relation with the cleaning assembly 20, the activation device 44 is disposed into an operative, activating relation with the reader assembly 40, and the reader assembly 40 is disposed into an operative state or otherwise turned on or activated such that a proximately disposed hygienic monitoring device 30 may be detected as described above. For instance, in at least one embodiment, upon disposition of the stethoscope 12 or head portion 14 in the cleaning relation with the cleaning assembly 20, the stethoscope 12 will engage one or more gate members 26, 28, which in turn will move levers 43 and thereby dispose the activating device 44 into its operative position (FIG. 4). Upon removal of the stethoscope 12 and/or head portion 14 from the cleaning relation or position, the gate member(s) 26, 28 become disengaged thereby disposing the levers 43 and the activating device 44 into a relaxed or non-operative state (FIG. 3). Upon doing so, the reader assembly 40 may automatically return to a non-operative, sleep mode or state, either instantaneously, in a predetermined amount of time, or when it is finished detecting, identifying, storing, communicating, or otherwise operating in its intended manner as discussed herein.

Furthermore, there may be times where the cleaning fluid or barriers of the cleaning assembly 20 need to be replenished, or when the cleaning assembly 20 malfunctions or otherwise fails to operate in its intended manner. In order to facilitate the detection and tracking of whether the cleaning assembly 20 in fact worked and applied cleaning fluid or a barrier to the head portion 14, or whether the cleaning assembly failed or malfunctioned, at least one embodiment of the stethoscope disinfection monitoring and reporting system 10 of the present invention comprises a cleaning verification assembly 48 connected to the housing 22 of the cleaning assembly 20 in a predetermined location and at least momentarily disposed proximate to the head portion 14 of the stethoscope 12 after application of cleaning fluid on the head portion 14. For instance, the cleaning verification assembly comprises a sensor device 49 or plate which is structured and disposed to sense or otherwise detect the presence of cleaning fluid located on the head portion 14 of the stethoscope 12. The sensor 49 comprises any one of a plurality of structures or devices capable of detecting cleaning fluid or solution, such as an alcohol-based cleaning fluid. The predetermined location of the verification assembly 48 and/or sensor 49 is defined as being along the path of travel and/or within the receiving portion 24 or channel of the cleaning assembly 20, and subsequent to or following the application of cleaning fluid onto the head portion 14. The verification assembly 48 is capable of facilitating the detection of whether the head portion 14 was in fact cleaned or disinfected, and communicating or storing data relating thereto.

Figure 6:
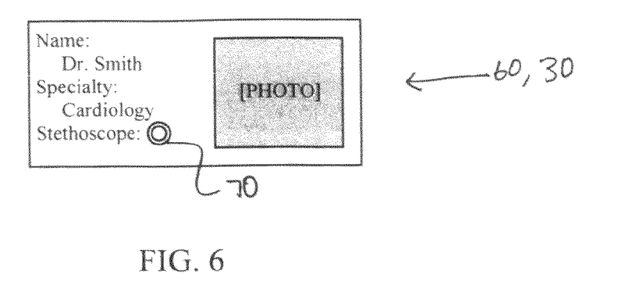
FIG. 6 is a schematic representation of an exemplary identification badge comprising a hygiene monitoring device and hygiene status indicator assembly as disclosed and described in accordance with at least one embodiment of the present invention.
Figure 7:
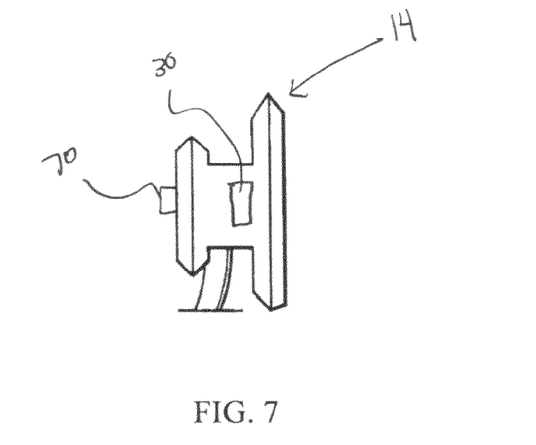
FIG. 7 is a partial side schematic representation of the head portion of a stethoscope comprising a monitoring device and a status indicator assembly as disclosed and described in accordance with at least one embodiment of the system 10.

Referring to FIGS. 6 and 7, the system 10 of at least one embodiment comprises a stethoscope hygiene status indicator assembly 70, which may be integrated with, connected to, or distinct and separate from the hygiene monitoring device 30. For instance, as illustrated in FIG. 6, a health care identification badge 60 may function as the hygiene monitoring device 30, with an integrated or connected hygiene status indicator assembly 70. However, as generally shown in FIG. 7, the hygiene status indicator assembly 70 may be separate from and not physically connected to the hygiene monitoring device 30.

Either way, the stethoscope hygiene status indicator assembly 70 is communicatively linked to the stethoscope cleaning data, which, as described above, is generally determinative or representative of a hygienic status of the stethoscope, or otherwise determinative of compliance with predetermined cleaning requirements. For instance, in at least one embodiment, the hygienic monitoring device 30 comprises memory capabilities structured to maintain updated cleaning data relating to the hygienic status of the associated stethoscope 12. The hygiene status indicator assembly 70 may be communicatively linked to the data by virtue of being integrated with and sharing the memory capabilities of the hygienic monitoring device 30, or wirelessly via wireless communication and may be implemented via 1-WIRE® connectors, smart buttons, Bluetooth, WiFi, ZIGBEE®, cellular, etc. In yet another embodiment, however, the hygiene status indicator assembly 70 and/or the hygiene monitoring device 30 disposable in a one-way or two-way communicative relation with the remote data collection system 50 via, for instance, via WiFi, Bluetooth, cellular, etc. In such an embodiment, the hygiene status indicator assembly 70 may be communicatively linked with the updated and current cleaning data stored on or otherwise maintained by the remote data collection system 50.

Moreover, the hygiene status indicator assembly 70 may comprise and indicator structured and disposed to discretely or non-discretely identify the current hygienic status of the associated stethoscope 12 via visual indicators, audible indicators, or motion indicators such as vibration. For example, at least one embodiment of the hygiene status indicator assembly 70 comprises a visual single or multi-colored LED indicator structured and disposed to visually identify the hygienic status of the associated stethoscope 12. For exemplary purposes only, the LED indicator may change from green, to yellow, to red, or other colors, indicating that the associated stethoscope is clean, recommended for cleaning, and must be cleaned, respectively. As represented in FIG. 6, the LED indicator may be disposed on the health care provider's identification badge 60 and capable of visual inspection or interpretation by virtually anyone, including the health care provider and his or her patient(s). Of course, the LED indicator or other hygiene status assembly 70 may also be located directly on the stethoscope itself, and be either fixedly or removably attached thereto.

The hygiene status indicator assembly 70 may also or instead comprise an audio indicator such as in the form of a speaker or other like device structured to emit a pre-recorded audible sound, beep, or other audible warnings or indications as to the hygienic status of the stethoscope 12. For instance the status indicator assembly 70 may emit a pre-recorded message such as "It's time to clean your stethoscope," or "Stop, clean your stethoscope before proceeding." However, a beep or multiple beeps may be emitted in order to warn or send a message to the physician(s) and/or patient(s).

Furthermore, in yet another embodiment the hygiene status indicator assembly 70 comprises a vibration or motion assembly structured to identify the hygienic status of the associated stethoscope 12. For instance, the vibration or motion assembly may discretely vibrate or move in order to warn the physician that the stethoscope 12 needs to be cleaned. Similar to the LED assembly, the vibration assembly may be integrated with the health care provider's identification badge 60 and/or connected to the stethoscope 12 itself, so as to vibrate the badge 60 or stethoscope 12, respectively.

Figure 8:
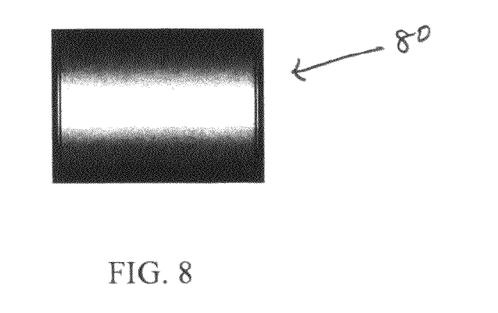
FIG. 8 is a schematic representation of a remote detection assembly of at least one embodiment of the present invention.

Additionally, yet another embodiment of the stethoscope disinfection monitoring and reporting system 10 of the present invention comprises a remote detection assembly 80 disposed at a predetermined remote location. The remote detection assembly 80 of the various embodiments may comprise a proximity sensor or other structures capable of detecting, communicating with, or sending a remote signal to other proximately disposed devices. The predetermined remote location may be defined as an area or location at or near a patient, such as, for example, a patient's room, on the patient or patient's identification badge, at or near a door leading into and/or out of the patient's room, at or near a door leading into and/or out of the medical facility, etc. Specifically, the remote detection assembly 80 is disposable in a communicative relation with the hygienic monitoring device 30 upon disposition of the hygienic monitoring device 30 in a predetermined or proximate relation thereto.

As identified above, it is recommended that the stethoscope 12 is cleaned at least once every three hours and prior to each use. Thus, when a physician or health care provider approaches a location proximate the remote detection assembly 80, for instance within a few feet, within the same room, or otherwise within a predetermined communication distance, the hygienic monitoring device 30 and the remote detection assembly 80 of at least one embodiment establish a communication channel or signal there between, at least to the extent of notifying the hygienic monitoring device 30 of the presence of a proximately disposed remote detection assembly 80.

In at least one embodiment, the hygiene status indicator assembly 70 is disposed in an activated state upon disposition of the hygienic monitoring device 30 and/or hygiene status indicator assembly 70 in a proximate relation with the remote detection assembly. For example, as provided above, the hygiene status indicator assembly 70 is communicatively linked, either directly or indirectly, to certain stethoscope cleaning data disposed on the hygienic monitoring device 30 and/or a remote data collection system 50, and is structured to provide a visual, audible, or vibration indication as to the hygienic status of the stethoscope 12. Accordingly, upon disposition of the hygienic monitoring device 30 and/or the status indicator assembly 70 in a predetermined proximate relation with one or more remote detection assemblies, the status indicator assembly 70 is activated and thus will indicate the hygienic status of the stethoscope 12, for example, via a vibration assembly, LED indicator, or audible sound. Of course, it is contemplated that the status indicator assembly 70 is only activated and/or only indicates when the stethoscope 12 is in need of a cleaning and may thus not emit an indication each time the hygienic monitoring device 30 and/or the status indicator assembly 70 is disposed in a proximate location with the remote detection assembly.

Furthermore, when a physician or health care provider approaches a patient and/or uses the stethoscope 12 on the patient, the stethoscope 12 must be cleaned prior to another subsequent use. Thus, the hygienic status of the stethoscope 12 may change or be modified upon disposition of the stethoscope 12 in a proximate or engaging relation with a patient. As such, in at least one embodiment, the hygienic monitoring device 30 and/or the remote data collection system 50 are structured to modify the stethoscope cleaning data, at least to the extent of the data being determinative or representative of the hygienic status of the stethoscope 12, upon disposition of the hygienic monitoring device 30 in a predetermined or proximate relation with the remote detection assembly 80. For instance, the hygienic monitoring device 30 of at least one embodiment comprises appropriate logic and/or functioning so as to detect a proximately disposed remote detection assembly 80, and modify the cleaning data disposed thereon to reflect or represent a hygienic status of dirty or needs cleaning. Of course, if the cleaning data is stored on the remote data collection system 50, the hygienic monitoring device 30 is capable of communicating a signal to the remote data collection system 50 to appropriately modify the hygienic status.

For exemplary purposes only, in the event a physician is carrying a "clean" or recently cleaned stethoscope 12 into a patient's room or otherwise proximate a remote detection assembly, the hygienic monitoring device will detect the presence of the remote detection assembly 80, and the status indicator assembly 70 will indicate that the stethoscope 12 is "clean," for example, via a green LED. By virtue of being proximate to the patient with the stethoscope 12, the hygienic status will change from "clean" to "needs cleaning" via modification of the cleaning data stored on the hygienic monitoring device 30 or at a remote data collection system 50. If the physician approaches another remote detection assembly 80 prior to disposing the stethoscope head portion 14 in a cleaning relation with the cleaning assembly 20, or otherwise prior to cleaning the stethoscope 12, then the hygienic status indicator assembly will appropriately indicate that the stethoscope 12 needs cleaning. However, upon disposition of the stethoscope head portion in a cleaning relation with the cleaning assembly 20, the hygienic status of the stethoscope will reflect or otherwise be representative of a "clean" stethoscope.

Of course, the various movement and activity of the stethoscope 12 and/or monitoring device 30 may be tracked and stored for future analysis and/or interpretation. For instance, each time the stethoscope is cleaned, or approaches a remote detection assembly 80, the time, location, hygienic status, etc., may be saved and recorded either directly on the monitoring device 30 or at a remote data collection system 50.

Moreover, in light of the above devices and assemblies, the cleaning assembly 20 further comprises a power source, either via conventional cables, plugs or outlets, or via removable, replaceable, or integrated batteries or battery packs. Either way, for safety and in order to eliminate or minimize the possibility of fire, explosion, or simple malfunctioning of the device, because the cleaning fluid or solution used may be flammable when exposed to a power source, the power source of the various embodiments of the present invention is disposed in a predetermined location separated and isolated from any cleaning fluid or solution used to clean the stethoscope 12.

In addition, the cleaning assembly 20 as used herein may comprise a combination of multiple cleaning assemblies capable of cleaning the stethoscope, as described above, as well as other medical devices, and/or hand washing. For instance, in addition to monitoring and reporting the cleaning or hygienic status of the stethoscope 12 and/or head portion 14 thereof, the cleaning assembly 20, monitoring device 30, etc. may also report, track, and monitor the physician's or health care provider's hand washing activities.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A stethoscope disinfection monitoring and reporting system, comprising:
a cleaning assembly comprising a housing sized to hang on a vertical surface and structured and configured to at least partially clean a head portion of a stethoscope,
a reader assembly connected to said housing at a predetermined location,
a hygienic monitoring device at least momentarily disposed in a proximate and communicative relation with said reader assembly while the head portion of the stethoscope is disposed in a cleaning relation to said cleaning assembly,
wherein said reader assembly is configured to be activated as a result of the head portion of the stethoscope being in said housing of said cleaning assembly for cleaning, and is structured and disposed to detect and identify said proximately disposed hygienic monitoring device only once activated,
a cleaning verification assembly connected to said housing and including a sensor device, said sensor device disposed in communicating relation to the head portion when the head portion is in said cleaning relation within said cleaning assembly, and
said sensor structured to detect and verify the presence of a cleaning fluid on the head portion of the stethoscope assembly when in said cleaning assembly.

2. The system as recited in claim 1 further comprising a remote data collection system; said remote data collection system comprising a storage assembly structured to store and maintain a plurality of stethoscope identification and cleaning data communicated thereto.

3. The system as recited in claim 2 wherein said cleaning assembly further comprises a wireless communication device.

4. The system as recited in claim 3 wherein said remote data collection system is disposed in a communicative relation with said wireless communication device of said cleaning assembly.

5. The system as recited in claim 4 wherein said remote data collection system is disposed in a data receiving relation with said wireless communication device of said cleaning assembly.

6. The system as recited in claim 4 wherein said wireless communication device of said cleaning assembly is structured to communicate said plurality of stethoscope identification and cleaning data to said remote data collection system.

7. The system as recited in claim 1 wherein said hygienic monitoring device is uniquely associated with the stethoscope.

8. The system as recited in claim 1 wherein said hygienic monitoring device is uniquely associated with a health care identification badge.

9. The system as recited in claim 1 further comprising a stethoscope hygiene status assembly communicatively linked to stethoscope cleaning data determinative of a hygienic status of the stethoscope.

10. The system as recited in claim 9 wherein said stethoscope hygiene status assembly comprises a visual LED indicator structured to identify the hygienic status of the stethoscope.

11. The system as recited in claim 9 wherein said stethoscope hygiene status assembly comprises a vibration assembly structured to identify the hygienic status of the stethoscope.

12. The system as recited in claim 1 wherein said cleaning assembly further comprises an activation device disposable into and out of an operative and activating relation with said reader assembly.

13. The system as recited in claim 12 wherein said activation device is structured to dispose said reader assembly into an operative state upon disposition of the head portion of the stethoscope into a cleaning relation with said cleaning assembly.

14. The system as recited in claim 1 further comprising a remote detection assembly disposed at a predetermined remote location; said remote detection assembly being disposable in a communicative relation with said hygienic monitoring device upon disposition of said hygienic monitoring device in a proximate relation to said remote detection assembly.

15. The system as recited in claim 14 further comprising a hygiene status indicator assembly communicatively linked to stethoscope cleaning data determinative of a hygienic status of the stethoscope.

16. The system as recited in claim 15 wherein said hygiene status indicator assembly is disposed into an activated state upon disposition of said hygienic monitoring device in said proximate relation to said remote detection assembly.

17. The system as recited in claim 16 wherein said hygienic monitoring device comprises memory capabilities structured to store said stethoscope cleaning data; said monitoring device being structured to modify said stethoscope cleaning data upon disposition of said hygienic monitoring device in a proximate relation with said remote detection assembly.

18. The system as recited in claim 16 further comprising a remote data collection system comprising a storage assembly structured to store said stethoscope cleaning data; said remote data collection system being disposed in a communicative relation with said hygienic monitoring device.

19. The system as recited in claim 18 wherein said remote data collection system is structured to modify said stethoscope cleaning data upon disposition of said hygienic monitoring device in a proximate relation with said remote detection assembly.

20. The system as recited in claim 1 wherein said hygienic monitoring device comprises a radio frequency identification (RFID) device.

21. The system as recited in claim 18 wherein said reader assembly comprises an RFID reader.

22. A stethoscope disinfection monitoring and reporting system, comprising:
   a cleaning assembly comprising a housing sized to hang on a vertical surface, said housing structured and configured to at least partially clean a head portion of a stethoscope,
   a reader assembly connected to said housing at a predetermined location,
   a hygienic monitoring device at least momentarily disposed in a proximate and communicative relation with said reader assembly while the head portion of the stethoscope is disposed in a cleaning relation within said cleaning assembly,
   said reader assembly structured and disposed to detect and identify said proximately disposed hygienic monitoring device,
   an activation device connected to said cleaning assembly and structured to dispose said reader assembly into and out of an operative, activating state, and
   said activating device further structured to be triggered by the stethoscopes passage in said housing and when triggered to dispose said reader assembly into said operative, activating state only upon disposition of the head portion of the stethoscope into said cleaning relation within said cleaning assembly and said cleaning assembly cleaning the head portion of the stethoscope.

23. The system as recited in claim 22 further comprising a cleaning verification assembly connected to said housing of said cleaning assembly in a predetermined location and at least momentarily disposed proximate to the head portion of the stethoscope.

24. The system as recited in claim 23 wherein said cleaning verification assembly comprises a sensor device structured to detect and verify the presence of cleaning fluid on the head portion of the stethoscope assembly.

* * * * *